(12) United States Patent
Turner et al.

(10) Patent No.: US 7,585,844 B2
(45) Date of Patent: Sep. 8, 2009

(54) MYOSIN LIGHT CHAIN KINASE INHIBITORS AND METHODS OF USE

(75) Inventors: Jerrold R. Turner, Wilmette, IL (US); Randall J. Mrsny, Los Altos Hills, CA (US)

(73) Assignees: The University of Chicago, Chicago, IL (US); University College Cardiff Consultants Ltd., Cardiff (GB)

( * ) Notice: Subject to any disclaimer, the term of this patent is extended or adjusted under 35 U.S.C. 154(b) by 445 days.

(21) Appl. No.: 11/111,463

(22) Filed: Apr. 21, 2005

(65) Prior Publication Data

US 2005/0261196 A1 Nov. 24, 2005

Related U.S. Application Data

(60) Provisional application No. 60/564,313, filed on Apr. 21, 2004.

(51) Int. Cl.
*A61K 38/08* (2006.01)
(52) U.S. Cl. .......................................... 514/15; 530/328
(58) Field of Classification Search ........................ None
See application file for complete search history.

(56) References Cited

U.S. PATENT DOCUMENTS

| 5,336,503 | A | 8/1994 | Wakasugi |
| 5,635,371 | A | 6/1997 | Stout et al. |
| 5,846,545 | A | 12/1998 | Chari et al. |
| 5,879,713 | A | 3/1999 | Roth et al. |
| 5,891,689 | A | 4/1999 | Takle et al. |
| 6,172,043 | B1 | 1/2001 | Ingram et al. |
| 6,673,574 | B2 | 1/2004 | Stern et al. |
| 6,777,388 | B1 * | 8/2004 | Grasso et al. ................. 514/16 |
| 2005/0042295 | A1 | 2/2005 | Hunter et al. |

FOREIGN PATENT DOCUMENTS

| WO | WO 97/13782 | 4/1997 |
| WO | WO 97/35873 | 10/1997 |
| WO | WO 03/089002 | 10/2003 |

OTHER PUBLICATIONS

Adessi, C. et al., "Converting a peptide into a drug: strategies to improve stability and bioavailability," Curr. Med. Chem. (2002) 9(9):963-978.
Ramanathan, S. et al., "Targeted PEG-based bioconjugates enhance the cellular uptake and transport of a HIV-1 TAT nonapeptide," J. Controlled Release (2001) 77(3):199-212.
Ramanathan, S. et al., "Targeting the sodium-dependent multivitamin transporter (SMVT) for improving the oral absorption properties of a retro-inverso TAT nonapeptide," Pharm. Res. (2001) 18(7):950-956.
Andersson et al., "Large-Scale Synthesis of Peptides," *Peptide Science* 55(3):227-250 (2000).
Anwer et al. "Backbone Modifications in Cyclic Peptides: Conformational Analysis of a Cyclic Pseudopentapeptide Containing a Thiomethylene Ether Amide Bond Replacement," *Int. J. Peptide Protein Res.* 36:392-399 (1990).
Arnott et al., "Abnormal Intestinal Permeability Predicts Relapse in Inactive Crohn Disease," *Scand. J. Gastroenterol* 35:1163-1169 (2000).
Barany G. & Merrifield, R. in *The Peptides* (E Gross and J. Meienhofer, eds.), Academic Press, New York, 2:1-284 (1979).
Bonen et al., "The Genetics of Inflammatory Bowel Disease," *Gasteroenterology* 124:521-536 (2003).
Burgess et al., DiSSiMiL: Diverse Small Size Mini-Libraries Applied to Simple and Rapid Epitope Mapping of a Monoclonal Antibody. *J. Peptide Res.*, 57:68-76 (2001).
Carty et al., "Evaluation of New Therapeutics for Inflammatory Bowel Disease," *Br. J. Clin. Pharmacol.* 56:351-361 (2003).
Chorev et al., "Recent Developments in Retro Peptides and Proteins—An Ongoing Topochemical Exploration," *Trends Biotechnol.* 13:438-445 (1995).
Chowdhury et al., "Fate of DNA Targeted to the Liver by Asialoglycoprotein Receptor-Mediated Endocytosis in vivo. Prolonged Persistence in Cytoplasmic Vesicles After Partial Hepatectomy," *J. Biol. Chem.* 268:15:11265-11271 (1993).
Counsell et al., "Lipoproteins as Potential Site-Specific Delivery Systems for Diagnostic and Therapeutic Agents," *J. Med. Chem.* 25:10:1115-1120 (1982).
Davis et al. in *Site-Specific Drug Delivery* (Tomlinson et al. eds.), John Wiley, NY (1986) 93-110.
Fasano et al., "Modulation of Intestinal Tight Junctions by Zonula Occludens Toxin Permits Enteral Administration of Insulin and Other Macromolecules in an Animal Model," *J. Clin. Invest.* 99:1158-1164 (1997).
Fields G.B., *Solid-Phase Peptide Synthesis*, San Diego Academic Press (1997).
Fullner et al., "*Vibrio cholerae*-Induced Cellular Responses of Polarized T84 Intestinal Epithelial Cells are Dependent on Production of Cholera Toxin and the TRX Toxin," *Infection & Immunity* 69(10):6310-6317 (2001).
Greenwald et al., *Crit. Rev.Ther. Drug Carrier Syst.* 17:101-161 (2000).
Harris et al.,"Novel Process for Modifying Pharmacokinetics," *Clin. Pharmacokinet.* 40(7):539- 551 (2001).
Hecht et al., "*Clostridium difficile* Toxin A Perturbs Cytoskeletal Structure and Tight Junction Permeability of Cultured Huma Intestinal Epithelial Monolayers," *J. Clin. Invest.* 82:1516-1524 (1988).
Hilsden et al., "Intestinal Permeability Changes in Response to Acetylsalicyclic Acid in Relatives of Patients with Crohn's Disease," *Gastroenterology* 110:1395-1403 (1996).
Hollander, D., "Crohn's Disease—A Permeability Disorder of the Tight Juncion?," *Gut* 29(12):1621-1624 (1988).
Kamm et al., "Dedicated Myosin Light Chain Kinases with Diverse Cellular Functions," *J. Biol. Chem.* 276(7):4527-4530 (2001).
Kopecek et al., "Water Soluble Polymers in Tumor Targeted Delivery," *J. Controlled Release* 74:1:3:147-158 (2001).

(Continued)

*Primary Examiner*—Anish Gupta
(74) *Attorney, Agent, or Firm*—Michael Best & Friedrich LLP

(57) ABSTRACT

Disclosed are inhibitors of myosin light chain kinase, pharmaceutical compositions and kits comprising the inhibitors and methods of use.

8 Claims, No Drawings

OTHER PUBLICATIONS

Lukas et al., "Identification of Novel Classes of Protein Kinase Inhibitors Using Combinatorial Peptide Chemistry Based on Functional Genomics Knowledge," *J. Med. Chem.* 42(5):910-919 (1999).

Madara, J.L., "Regulation of the Movement of Solutes Across Tight Junctions," *Ann. Rev. Physiol.* 60:143-159 (1998).

May et al., "Is Small Intentinal Permeability Really Increased in Relatives of Patients with Crohn's Disease?" *Gastroenterology* 104:1627-1632 (1993).

Merrifield, R.B., "Solid Phase Synthesis," *Science* 232:341-347 (1986).

Musch et al., "T Cell Activation Causes Diarrhea by Increasing Intestinal Permeability and Inhibiting Epithelial NA+/K+-ATPase.," *J. Clin. Invest.* 110:1739-1747 (2002).

Nachman et al., "Pseudodipeptide Analogs of the Pyrokinin/PBAN (FXPRLa) Insect Neuropeptide Family Containing Carbocyclic Pro-Mimetic Conformational Components," *Regulatory Peptides*, 57(3):359-370 (1995).

Nathan et al., "Hydrogels Based on Water-Soluble Poly(ether urethanes) Derived from L-Lysine and Poly(ethylene glycol)," *Macromolecules* 25: 4476-4484 (1992).

Nathan et al., "Copolymers of Lysine and Polyethylene Glycol: A New Family of Functionalized Drug Carriers," *Bioconj. Chem.* 4:54-62 (1993).

Nusrat et al., "Molecular Physiology and Pathophysiology of Tight Junctions IV., Regulation of Tight Junctions by Extracellular Stimuli: Nutrients, Cytokines and Immune Cells," *Am. J. Physiol Gatrointest Liver Physiol.* 279:G851-G857 (2000).

Nusrat et al., "*Clostridium difficile* Toxins Disrupt Epithelial Barrier Function by Altering Membrane Microdomain Localization of Tight Junction Proteins," *Infect. Immun.* 69(3):1329- 1336 (2001).

Pearson et al., "Substrate Specificity of a Multifunctional Calmodulin-Dependent Protein Kinase," *J. Biol. Chem.* 260(27):14471-14476 (1985).

"Peptides for the New Millennium," G.B. Fields, J.P. Tam & G. Barany (eds.), Kluwer Academic Publishers (2000).

Philpott et al., "Signal Transduction Pathways Involved in Enterohemorrhagic *Escherichia coli*-Induced Atterations in T84 Epithelial Permeability," *Infection & Immunity* 66:1680-1687 (1998).

Poznansky et al., "Biological Approaches to the Controlled Delivery of Drugs: A Critical Review," *Pharmacol. Rev.* 36(4):277-336 (1984).

Pritsker et al., "A Synthetic All D-Amino Acid Peptide Corresponding to the N-Terminal Sequence of HIV-1 gp41 Recognizes the Wild-Type Fusion Peptide in the Membrane and Inhibits HIV-1 Envelope Glycoprotein-Mediated Cell Fusion," *Proc. Natl. Acad. Sci. USA* 95:7287-7292 (1998).

Rivera-Baeza et al., "Backbone-to-Backbone Cyclized and Linear Pseudopeptide Analogs of Substance P as Ligands to the Substance P Receptor from Rat Brain," *Neuropeptides* 30(4):327- 333 (1996).

Sadowski et al., "Luminal Nutrients Alter Tight-Junction Permeability in the Rate Jejunum: An in vivo Perfusion Model.," *Can. J. Physiol. Pharmacol.* 71:835-839 (1993).

Sandler et al., "The Burden of Selected Digestive Diseases in the United States," *Gastroenterology.* 122:1500-1511 (2002).

Soderling et al., "Structure and Regulation of Calcium/Calmodulin-Dependent Protein Kinases," *Chem. Rev.* 101:2341-2351 (2001).

Spitz et al., "Enteropathogenic *Escherichia coli* Adherence to Intestinal Epithelial Monolayers Diminishes Barrier Function," *Am. J. Physiol. Gastrointest Liver Physiol* 268:G374-G379 (1995).

Stewart & Young, *Solid Phase Peptide Synthesis* ($2^{nd}$ ed.), Pierce Chemical Co., Rockford III, (1984).

Tafazoli et al., "Apically Exposed, Tight Junction-Associated β1-Integrins Allow Binding and YopE-Mediated Perturbation of Epithelial Barriers by Wild-Ty;e *Yersinia* Bacteria," *Infection & Immunity* 68:5335-5343 (2000).

Tam et al., *J. Am. Chem. Soc.* 10(5):6442 (1983).

Teahon et al., "Intestinal Permeability in Patients with Crohn's Disease and Their First Degree Relatives," *Gut* 33:320-323 (1992).

Tiller, et al., "Fast LC/MS in the Analysis of Small Molecules," *Anal. Bioanal Chem.* 377:5:788-802 (2003).

Tomson et al., "Differing Roles of Protein Kinase C-Zeta in Disruption of Tight Junction Barrier by Enteropathogenic and Enterohemorrhagic *Escherichia coli*," *Gastroenterology* 127:3:859-69 (2004).

Turner et al., "Protein Kinase C-Dependent Regulation of Transepithelial Resistance: The Roles of Myosin Light Chain and Myosin Light Chain Kinase," *Am. J. Physiol.* 277:C554-0562 (1999).

Turner et al., "Physiological Regulation of Epithelial Tight Junctions is Associated with Myosin Light-Cahin Phosphorylation," *Am. J. Physiol.* 273:C1378-C1385 (1997).

Wainright et al., "Protein Kinase Involved in Lung Injury Susceptibility: Evidence from Enzyme Isoform Genetic Knockout and in vivo Inhibitor Treatment," *Proc.Nat. Acad. Sci. USA* 100:10:6233-6238 (2003).

Wittchen et al., "Protein Interactions at the Tight Junction Actin has Multiple Binding Partners, and ZO-1 Forms Independent Complexes with ZO-2 and ZO-3," *J. Biol. Chem.* 274:35179- 35185 (1999).

Zalipsky et al., "Poly(ethylene glycol)-Grafted Liposomes with Oligopeptide or Oligosaccharide Ligands Appended to the Termini of the Polymer Chains," *Bioconjug. Chem.* 8:111-118 (1997).

Zolotarevsky et al. "A Membrane-Permeant Peptide that Inhibits MLC Kinase Restores Barrier Function in in vitro Models of Intestinal Disease," *Gastroenterology* 123:1:163-172 (2002).

* cited by examiner

SEQUENCE LISTING

<160> NUMBER OF SEQ ID NOS: 14

<210> SEQ ID NO 1
<211> LENGTH: 22
<212> TYPE: PRT
<213> ORGANISM: Homo sapiens

<400> SEQUENCE: 1

Ala Lys Lys Leu Ser Lys Asp Arg Met Lys Lys Tyr Met Ala Arg Arg
1               5                   10                  15

Lys Trp Gln Lys Thr Gly
            20

<210> SEQ ID NO 2
<211> LENGTH: 22
<212> TYPE: PRT
<213> ORGANISM: Ovis aries

<400> SEQUENCE: 2

Ala Lys Lys Leu Ser Lys His Arg Met Lys Lys Tyr Met Ala Arg Arg
1               5                   10                  15

Lys Trp Gln Lys Thr Gly
            20

<210> SEQ ID NO 3
<211> LENGTH: 22
<212> TYPE: PRT
<213> ORGANISM: Tetraodon nigroviridis

<400> SEQUENCE: 3

Ala Lys Lys Leu Ser Lys Glu Arg Met Lys Lys Tyr Ile Leu Arg Arg
1               5                   10                  15

Lys Trp Gln Lys Thr Gly
            20

<210> SEQ ID NO 4
<211> LENGTH: 22
<212> TYPE: PRT
<213> ORGANISM: Carassius auratus

<400> SEQUENCE: 4

Val Lys Lys Leu Ser Lys Glu Arg Met Lys Lys Tyr Ile Leu Arg Arg
1               5                   10                  15

Lys Trp Gln Lys Thr Gly
            20

<210> SEQ ID NO 5
<211> LENGTH: 22
<212> TYPE: PRT
<213> ORGANISM: Canis familiaris

<400> SEQUENCE: 5

Ala Lys Lys Leu Ser Lys Asp Arg Met Lys Lys Tyr Met Ala Arg Arg
1               5                   10                  15

Lys Trp Gln Lys Arg Lys
            20

<210> SEQ ID NO 6
<211> LENGTH: 22
<212> TYPE: PRT
<213> ORGANISM: Artificial sequence

```
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid

<400> SEQUENCE: 6

Xaa Lys Lys Leu Ser Lys Xaa Arg Met Lys Lys Tyr Xaa Xaa Arg Arg
1               5                   10                  15

Lys Trp Gln Lys Xaa Xaa
            20

<210> SEQ ID NO 7
<211> LENGTH: 11
<212> TYPE: PRT
<213> ORGANISM: Homo sapiens

<400> SEQUENCE: 7

Tyr Gly Arg Lys Lys Arg Arg Gln Arg Arg
1               5                   10

<210> SEQ ID NO 8
<211> LENGTH: 26
<212> TYPE: PRT
<213> ORGANISM: Kaposi's virus fibroblast growth factor

<400> SEQUENCE: 8

Ala Ala Val Ala Leu Leu Pro Ala Val Leu Leu Ala Leu Leu Ala Pro
1               5                   10                  15

Val Asn Arg Lys Arg Asn Lys Leu Met Pro
            20                  25

<210> SEQ ID NO 9
<211> LENGTH: 15
<212> TYPE: PRT
<213> ORGANISM: Homo sapiens

<400> SEQUENCE: 9

Val Thr Val Leu Ala Leu Gly Ala Leu Ala Gly Val Gly Val Gly
1               5                   10                  15

<210> SEQ ID NO 10
<211> LENGTH: 34
<212> TYPE: PRT
<213> ORGANISM: Herpes simplex virus VP22 protein transduction domain

<400> SEQUENCE: 10

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu
```

```
<210> SEQ ID NO 11
<211> LENGTH: 16
<212> TYPE: PRT
<213> ORGANISM: Drosophila melanogaster

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 9
<212> TYPE: PRT
<213> ORGANISM: Artificial sequence
<220> FEATURE:
<223> OTHER INFORMATION: Synthetic oligonucleotide

<400> SEQUENCE: 12

Arg Lys Lys Tyr Lys Tyr Arg Arg Lys
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic oligonucleotide

<400> SEQUENCE: 13

Lys Arg Arg Tyr Lys Tyr Lys Lys Arg
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: Xaa can be any naturally occurring amino acid

<400> SEQUENCE: 14

Xaa Xaa Xaa Xaa Xaa Xaa Xaa Xaa Xaa
1               5
```

MYOSIN LIGHT CHAIN KINASE INHIBITORS AND METHODS OF USE

CROSS-REFERENCE TO RELATED APPLICATIONS

This application claims the benefit of U.S. Provisional Application No. 60/564,313, filed Apr. 21, 2004.

STATEMENT REGARDING FEDERALLY SPONSORED RESEARCH

This invention was made with United States government support awarded by the National Institutes of Health Grant No. DK 61931. The government has certain rights in the invention.

INTRODUCTION

This invention relates to inhibitors of myosin light chain kinase ("MLCK"). Myosin light chain kinase catalyses the phosphorylation of myosin light chain (MLC) in the presence of $Ca^{2+}$/calmodulin and ATP, and regulates the contraction of actomyosin, which is involved in a broad range of cellular activities, some of which may be implicated in disease states. MLCK inhibitors may be useful in treating or ameliorating such disease states.

SUMMARY OF THE INVENTION

In one aspect, the present invention provides an inhibitor of myosin light chain kinase is provided having the general formula A-B-C wherein B is covalently bonded to A and C and wherein A and C each comprise at least two basic amino acids; and B comprises Xaa1-Xaa2-Xaa3 wherein Xaa1, Xaa2 and Xaa3 are amino acids as described hereinbelow. The inhibitor includes at least one amino acid that is a D-amino acid, or includes at least one non-hydrolyzable bond.

In one particular embodiment, the invention provides an inhibitor of myosin light chain kinase comprising a nonapeptide wherein the first three amino acids and last three amino acids of the sequence comprise basic amino acids, and wherein the inhibitor comprises at least one D-amino acid or at least one non-hydrolyzable bond.

In another aspect, the invention provides a pharmaceutical composition including an inhibitor of MLCK. Methods are also provided for inhibiting the phosphorylation of MLC, altering the permeability of epithelial monolayers, inhibiting cell migration, inhibiting the growth of tumors, inhibiting cell purse-string wound closure or inhibiting angiogenesis. In a further aspect, the invention provides methods to treat a variety of diseases, associated with MLCK activity.

DETAILED DESCRIPTION OF THE PREFERRED EMBODIMENTS

Myosin light chain kinase (MLCK) regulates actomyosin contraction, which is involved in a variety of cellular activities, including regulation of epithelial tight junctions (TJ), cell migration, purse-string wound closure, and muscle contraction.

It is contemplated that the compounds and compositions of the present invention may be used to treat of a variety of disorders associated with MLCK activity. Inhibitors of the invention may be used to treat any disorder that is caused by or exacerbated by MLCK-mediated actomyosin contraction within cells. The inhibitors of the instant invention may be used in a variety of therapeutic applications. Examples of conditions or disorders in which the inhibitors of the instant invention may have therapeutic value include, but are not limited to, intestinal diseases, such as infectious, ischemic, and idiopathic inflammatory diseases as well as graft v. host disease; diseases caused by infectious agents, including enteropathogenic *E. Coli* (EPEC), enterohemorrhagic *E. Coli* (EHEC), *Vibrio Cholerae, Yersinia, Clostridium difficile*, and *Shigella flexineri*; diseases of endothelial leak, such as sepsis, shock, anaphylaxis, and acute lung injury; diseases associated with smooth muscle contraction, such as asthma and hypertensive disease; diseases associated with cell migration, such as inflammation and tumor metastasis; diseases associated with angiogenesis, such as cancer, tumor-related diseases, cardiac disease, diabetic retinopathy; and diseases associated with platelet aggregation, such as thrombotic disease.

Intestinal diseases are generally linked to increased intestinal permeability. Phosphorylation of the myosin II regulatory light chain (MLC) is associated with increased intestinal epithelial TJ permeability. Infectious agents, including enteropathogenic bacteria, can also alter paracellular permeability.

Crohn's disease and ulcerative colitis are chronic disorders of the intestines, collectively known as inflammatory bowel disease and are linked to increased intestinal permeability. Intestinal permeability is increased in patients with active and inactive Crohn's disease and in a significant subset of their first degree relatives (May et al., *Gastroenterology* 1993; 104:1627-1632; Teahon et al., *Gut* 1992; 33:320-323). Inflammatory bowel disease has a familial link and several inflammatory bowel disease-related genes have been identified. Increased intestinal permeability is a prognostic marker for disease course because reactivation of inactive Crohn's disease is preceded by increased intestinal permeability (Arnott et al., *Scand J Gastroenterol* 2000; 35:1163-1169). These data suggest that increased intestinal permeability is an early event in the pathogenesis of Crohn's disease.

Graft versus host disease is also linked with increased intestinal permeability. Graft versus host disease is caused by mature donor T-cells that are activated by alloantigens expressed by the host antigen-presenting cells. The increased intestinal permeability and diarrhea which may be due to an increase in cytokines, such as TNF-α.

MLCK inhibitors may be effective at inhibiting tumor metastasis by either reducing cell migration or by directly killing or wounding tumor cells. In accordance with the present invention, when effective amounts of an MLCK inhibitor are administered to patients with cancer or neoplasms, or to tumors, the proliferative activity of the abnormal neoplastic cells is inhibited, reduced, or stabilized.

Vertebrates have at least two MLCK genes: skeletal muscle MLCK and smooth muscle MLCK. Smooth muscle MLCK is ubiquitously found in adult tissues, whereas skeletal muscle MLCK is tissue specific. Vertebrates express a short and long form of MLCK, as well as a related C-terminal Ig module: the non-kinase protein telokin. The short form MLCK includes a catalytic core, a regulatory sequence containing an autoinhibitory and $Ca^{2+}$/calmodulin binding domain, and an actin-binding sequence at the N terminus. The long form MLCK includes the domains of the short form and also an N-terminal extension with additional actin-binding motifs. The long form MLCK is not normally expressed in smooth muscle cells, and is also known as the 210-KDa, nonmuscle or endothelial MLCK. MLCK is regulated by intramolecular interactions between the catalytic domain and the autoinhibitory domain. The inhibitory domain, along with other peptides reported to have MLCK-inhibitory ability tend to be recognized and cleaved by proteases, particularly those of the stomach and intestine.

In one embodiment, the present invention provides MLCK inhibitors that inhibit the activity of MLCK, are resistant to degradation by proteases, and exhibit stability in vivo. More preferably, the inhibitors of the present invention show specificity for the inhibition of MLCK over other kinases and/or are designed to resist degradation by a protease. Inhibitors that inhibit the MLCK expressed within endothelial, epithelial, other non-muscle cells, or smooth muscle cells are provided.

An inhibitor of MLCK according to the present invention is one that inhibits phosphorylation of MLC or prevents or reduces actomyosin contraction. As described in the examples below, inhibitors can be assayed using an in vitro assay comprising the substrates MLC and γ-ATP. The effects of the inhibitor administered to a cell or epithelial layer of cells comprising MLCK can be measured biochemically, through imaging or by its correlation with a decrease in the transepithelial resistance (TER). Furthermore, the flux of labeled metabolites, such as $^3$H-mannitol, across a monolayer of epithelial cells in the presence or absence of a putative MLCK inhibitor can be measured, and used as an assay of the effectiveness of the inhibitor (Zolotarevsky et al., Gasteroenterology 124, 163-172, 2002).

As used herein, an inhibitor may be a peptide or a peptide mimetic that prevents phosphorylation of myosin light chain by MLCK. A peptide inhibitor of the instant invention may comprise L-amino acids, D-amino acids or a combination of L-amino acids and D-amino acids.

Preferred inhibitors of the instant invention have the general formula

A-B-C wherein B is covalently bonded to A and C, and wherein A and C each comprise at least two basic amino acids and B comprises at least three amino acids Xaa1, Xaa2 and Xaa3. Suitably, A and C may each comprise at least three basic amino acids. The preferred inhibitor A-B-C further comprises at least one D-amino acid, or a non-hydrolyzable bond.

In a preferred embodiment, Xaa1 of B is selected from the group consisting of Tyr, Val, Lys, Gln, Phe, Ser, Pro, Thr, Asn, and Arg; Xaa2 is covalently bonded to Xaa1, and is selected from the group consisting of Lys, Val, Thr, Trp, His, Met, Asn, Ala, Glu, Phe, Gln, and Arg; and Xaa3 is covalently bonded to Xaa2, and is selected from the group consisting of Ala, Asp, Glu, Phe, Gly, Lys, Leu, Met, Asn, Pro, Gln, Arg, Ser, Thr, Val, and Tyr.

In one embodiment, Xaa1 of B is selected from the group consisting of Tyr, Val, Lys, Gln, and Phe; Xaa2 is selected from the group consisting of Lys, Val, Thr, Trp, and His; and Xaa3 is selected from the group consisting of Tyr, Met, Pro, Ser and Phe.

In a particularly preferred embodiment, B comprises a sequence selected from the group consisting of Tyr-Lys-Ala, Tyr-Lys-Asp, Tyr Lys-Glu, Tyr-Lys-Phe, Tyr-Lys-Gly, Tyr-Lys-Lys, Tyr-Lys-Leu, Tyr-Lys-Met, Tyr-Lys-Asn, Tyr Lys-Pro, Tyr-Lys-Gln, Tyr-Lys-Arg, Tyr-Lys-Ser, Tyr-Lys-Thr, Tyr-Lys-Val and Tyr-Lys-Tyr.

In a preferred embodiment, A and C each comprise arginine, lysine or a combination thereof. In preferred inhibitors, the covalent bonds between B and A, and between B and C, or between Xaa2 and Xaa1, and Xaa2 and Xaa3 are peptide bonds.

As used herein, a non-hydrolyzable bond is one that resists hydrolysis by an enzyme (e.g., a protease). One of skill in the art will appreciate that non-hydrolyzable bonds may be hydrolyzed if subjected to extreme conditions, such as heating in a strong base or acid. However, such hydrolysis is outside the scope of the term non-hydrolyzable as used herein.

It may be desirable to prevent the degradation of the inhibitors. Degradation of the inhibitor may be prevented by including a non-hydrolyzable peptide bond. Such bonds, and methods for synthesizing peptides containing such bonds, are known in the art. Examples of non-hydrolyzable bonds include, but are not limited to, thioxo peptide bonds, reduced amide peptide bonds, ketomethylene peptide bonds, (cyanomethylene)amino peptide bonds, hydroxyethylene peptide bonds, and thiomethylene peptide bonds (see e.g., U.S. Pat. No. 6,172,043, herein incorporated by reference). Structures of certain non-hydrolyzable peptide bonds are shown in Table 1.

TABLE 1

| Type of Bond | Structure |
|---|---|
| thioxo peptide bond | —C(=S)—NH— |
| reduced amide peptide bond | —CH$_2$—NH— |
| ketomethylene peptide bond | —C(=O)—CH$_2$— |
| (cyanomethylene)amino peptide bond | —CH(CN)—NH— |
| hydroxyethylene peptide bond | —CH$_2$—CH(OH)— |
| thiomethylene peptide bond | —CH$_2$—S— |

It is further understood that any numerical value recited herein includes all values from the lower value to the upper value. For example, if a peptide is stated as having 7 to 300 amino acids, it is intended that values such as 7 to 25, 8 to 30, 9 to 90 or 50 to 300 are expressly enumerated in this specification. These are only examples of what is specifically intended, and all possible combinations of numerical values between the lowest value and the highest value enumerated are to be considered to be expressly stated in this application.

The peptide inhibitors in accordance with the present invention may comprise one or more D-amino acids. As demonstrated in the examples below, an MLCK inhibitor comprising 100% D-amino acids has a longer half-life in the presence of rat intestinal fluid in comparison to a peptide of comparable length comprising L-amino acids. It is envisaged that a peptide comprising less than 100% D-amino acids would also resist proteolysis.

It is also envisioned that by adjusting the proportion of D-amino acids contained within an inhibitor, one of ordinary skill in the art could identify an MLCK inhibitor having a half life intermediate to that of an inhibitor having all D-amino acids and an inhibitor having all L-amino acids. Inhibitors useful in applications where an intermediate half life is desired may have from 10% to 100% D-amino acids. Preferably, the MLCK inhibitor would have a sufficient number of D-amino acids to resist proteolysis, which property could be measured using any suitable method, e.g., as described in the examples.

MLCK-inhibiting compounds may be based on an intramolecular inhibition domain of smooth muscle MLCK. A preferred inhibition domain has the sequence from human MLCK (SEQ ID NO: 1). Based on a comparison of MLCK inhibition domains from *Ovis aries* (SEQ ID NO: 2), *Tetraodon nigroviridis* (SEQ ID NO: 3), *Carassius auratus* (SEQ ID NO: 4), and *Canis familiaris* (SEQ ID NO: 5), a consensus sequence can be derived (Xaa-Lys-Lys-Leu-Ser-Lys-Xaa-Arg-Met-Lys-Lys-Tyr-Xaa-Xaa-Arg-Arg-Lys-Trp-Gln-Lys-Xaa-Xaa; SEQ ID NO: 6) wherein each Xaa represents any natural or modified amino acid.

While in preferred embodiments, the MLCK inhibition domain sequence used herein is derived from human MLCK, it is contemplated that the sequence also may be derived from another mammalian source, or from the consensus sequence described above (SEQ ID NO: 6). In particularly preferred embodiments, the peptide inhibitor comprises the reverse of a contiguous sequence of the inhibitory domain.

The peptide inhibitors of the present invention can contain one or more variations in the sequence of the inhibitory domain. Such variants can be synthesized and tested for MLCK kinase activity. (Lukas et al., J. Med. Chem. 42, 910-919, 1999). Thus, inhibitors of the present invention include peptides comprising any number from 7 to 22 contiguous amino acids of the MLCK inhibitory domain, or the reverse thereof. Particularly preferred peptides comprise SEQ ID NO: 12 or SEQ ID NO: 13, wherein one or more of the amino acids are D-amino acids, or the sequences contain one or more non-hydrolyzable bonds.

Suitably, in a nonapeptide MLCK inhibitor from 1 to 9 of the amino acids are D-amino acids. In a particularly preferred embodiment, the MLCK inhibitor containing all D-amino acids is the reverse (N-terminus to C-terminus) of a MLCK inhibitor containing all L-amino acids. A reverse sequence means that the C-terminal amino acid becomes the N-terminal amino acid of the reverse sequence, with the remaining amino acids following in reverse order. By way of example, the reverse of the sequence FLM is MLF.

It is envisaged that the central amino acid residue (the lysine at position 5) of either SEQ ID NO: 12 or SEQ ID NO: 13 could be substituted with any amino acid residue and still function to inhibit MLCK.

It is also envisaged that the central three-amino-acid palindrome (the tyrosine-lysine-tyrosine residues at positions 4, 5 and 6) of either SEQ ID NO: 12 or SEQ ID NO: 13 could be substituted with any amino acid residue and still function to inhibit MLCK.

It is further envisaged that a peptide comprising a sequence of nine or more amino acids, such as SEQ ID NO: 14, wherein a central region of the sequence (amino acids at position 4, 5 and 6 of SEQ ID NO: 14) is flanked by sequences comprising two or more, or three or more, basic amino acids is also within the scope of the invention. In a preferred embodiment, the central region consists of three amino acids and the flanking regions each comprise three basic amino acids. In this embodiment, the central region may further comprise two tyrosine residues, each tyrosine residue flanking a central amino acid.

It is envisaged that the selection of different amino acids within the central region of the peptide inhibitor will result in inhibitors having a range of MLCK inhibitory activities, which can be tailored for use in different therapeutic situations, or which can be used to regulate the phosphorylation of myosin light chain according to a particular need.

The peptide inhibitors used in the present invention may be peptides of between 7 and 300 or more amino acid residues in length. The fragments that will be useful may be of any length from 7 amino acids in length to about 300 amino acids in length.

As used herein, an amino acid is meant to refer to a molecule that contains an amino group and a carboxylic acid group. An amino acid may be a natural amino acid or a non-natural amino acid. Natural amino acids are those commonly found in naturally occurring proteins. Non-natural amino acids include amino acids not commonly found in naturally occurring proteins, such as modified amino acids.

Modified amino acids include, for example, 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine, or ornithine.

In addition to the general structure A-B-C defined above, a peptide inhibitor may comprise a sequence that functions to allow the inhibitor to passively cross the cell membrane. It is envisaged that the peptide inhibitors may further comprise targeting sequences that facilitate the entry of the inhibitor into a cell. By way of example, such targeting sequences may include, but are not limited to, the transduction domain of HIV TAT protein (SEQ ID NO: 7), the signal peptide from Kaposi Fibroblast Growth Factor ( SEQ ID NO: 8), the signal sequence of human integrin beta₃ (SEQ ID NO: 9), the HSV-VP22 protein transduction domain (SEQ ID NO: 10), the antennapedia *Drosophila* homeotic transcription factor (SEQ ID NO: 11), flock house virus coat proteins, or peptides from basic leucine zipper segments of DNA binding proteins, such as c-Fos, c-Jun, and GCN4.

The MLCK inhibitors may also be linked to a ligand or carrier that has a high affinity for a particular cell type, tissue or organ and thereby facilitates targeted delivery to that cell type, tissue or organ. A targeting carrier is suitably one that increases delivery of the MLCK inhibitor to a desired target (e.g., a targeted cell, a targeted organ, a targeted component of a tissue of interest, a tumor, etc.). The targeting carriers suitably include chemical functionalities exhibiting target specificity, e.g., hormones (e.g., biological response modifiers), and antibodies (e.g., monoclonal or polyclonal antibodies), or antibody fragments having the requisite target specificity, e.g., to specific cell-surface antigens. A number of carriers such as monoclonal antibodies and colloidal delivery systems such as liposomes and polymeric microspheres or microcapsules formed of biocompatible polymers are known in the art. See, e.g., Davis et al. in *Site-Specific Drug Delivery*, (Tomlinson et al. eds.), John Wiley, New York, 1986, p.93; Roth et al., U.S. Pat. No. 5,879,713. Use of Hepatoptes (Charodhury, N. L., et al., *J. Biol. Chem.* 268, 11265 (1993)) and immunoliposomes has also been reported. Soluble molecules, including oligonucleotides, lectins, poly-L-lysine, virosomes, insulin, dextrans, HCG, dipeptides, lipoproteins and cellular systems such as erythrocytes and fibroblasts may facilitate the delivery of MLCK inhibitors to a target cell or tissue. See, e.g., Poznansky et al., 36 *Pharmacol. Rev.* 277 (1984); Counsell et al., 25 *J. Med. Chem.* 1115 (1982); Takle, et al., U.S. Pat. No. 5,891,689; Chari et al., U.S. Pat. No. 5,846,545.

Tumor-seeking carriers include certain antibodies, such as antibodies for vascular permeability factor and monoclonal antibodies, oxidized glycosylated proteins, polylysine, human serum albumin, dextrans, peptides and proteins that have an affinity for particular receptors, such as gastrin releasing peptide receptor, epidermal growth factor receptor, platelet-derived growth factor receptor, tumor necrosis factor receptor, fibroblast growth factor receptor, insulin-like growth factor receptor, transfertin receptor, laminin receptor, cytokine receptors, fibronectin receptor, interleukin receptor, interferon receptors, bombesen/gastrin-releasing peptide receptor, somastation receptor, etc., polyanionic compounds and polymers, such as sumarin and analogues and derivatives of sumarin, polysulphated compounds and polymers, such as heparin, heparan sulfate, chrondroitin sulfate, keratan sulfate, dermatan sulfate, sulfated chitin, sulfated chitosan, sulfated alginic acid, pentosan polysulfate, sulfated cyclodextrins, and synthetic organic polymers including polystyrene sulfonate, sulfated polyvinyl alcohol, polyvinyl sulfate, and polyethylene sulfonate, and analogs of peptide hormones, such as LH-RH, dombesin, and somatostatin.

Endothelial-targeting carriers may include CD31 antibodies. Bone-targeting carriers may include molecules such as bisphosphonates, estrogens and other steroids, such as dehydroepiandrosterone (DHEA), tetracycline, and polymalonates. Skin-seeking carriers include certain metal ion-amino acid chelates; prostate-seeking molecules include certain steroids such as DHEA. Liver-seeking carriers include triglycerides, particularly medium-chain triglycerides.

Inhibitors useful in the invention can be linear, or may be circular or cyclized by natural or synthetic means provided that the inhibitors retain MLCK-inhibitory activity. For example, disulfide bonds between cysteine residues may cyclize a peptide sequence. Bifunctional reagents can be used to provide a linkage between two or more amino acids of a peptide. Other methods for cyclization of peptides, such as those described by Anwer et al. (Int. J Pep. Protein Res. 36:392-399, 1990) and Rivera-Baeza et al. (Neuropeptides 30:327-333, 1996) are also known in the art.

Inhibitors may be obtained by conventional automated peptide synthesis methods, as described in the examples, or may be ordered commercially from providers of custom peptides. General principles for designing and making proteins are well known to those of skill in the art.

The inhibitors can be synthesized in solution or on a solid support in accordance with conventional techniques. The inhibitors can be prepared from a variety of synthetic or enzymatic schemes, which are well known in the art. Where short inhibitors are desired, such inhibitors may be prepared using automated peptide synthesis in solution or on a solid support in accordance with conventional techniques.

The inhibitors also may be modified, and such modifications may be carried out on the synthesizer with very minor interventions. An amide could be added at the C-terminus of the inhibitor. An acetyl group, biotin, stearate and other modifications could be added to the N-terminus. Other modifications may include adding a moiety to the inhibitor that would enable the inhibitor to covalently bond to MLCK, such that inhibition of the MLCK molecule would be irreversible. Suitably, the inhibitor can be synthesized to contain one or more D amino acids. Methods of producing peptides containing D amino acids are well known in the art (Pritsker et al., PNAS USA 95; 13:7287-7292).

Peptide mimetic inhibitors of MLCK are also envisaged. Peptide mimetics are generally known in the art. Preferably, the peptide mimetic inhibitors of MLCK have a secondary structure like the peptide MLCK inhibitors, with optional further structural characteristics. Peptide mimetic inhibitors can be prepared based on a peptide inhibitor by replacing one or more amino acid residues with a non-natural amino acid. Preferably, the non-natural amino acid permits the peptide mimetic to retain its confirmation, or stabilizes a preferred, e.g., bioactive confirmation and has an overall positive charge. Nonpeptide mimetic analogs from peptides can be prepared as described in Nachman et al., Regul. Pept. 57:359-370 (1995).

Examples of peptide mimetics are scaffold mimetics, non-peptidic mimetics, peptoids, azapeptides, oligocarbamates, oligopyrrlidones, oligoureas, vinylogous sulfonamidopeptides, β-peptides, and γ-peptides.

Scaffold mimetics, for example, include molecules such as chromone, isochromanone, diketopiperazine and pyridine derivatives Peptoids, for example, may contain a diversity of alkyl, aromatic, heterocyclic, cationic, and anionic N-substituents, such as N-substituted glycine. Peptoids are structurally similar to α-amino-acid polymers, but their backbone lacks chiral centers and hydrogen bond donors. Robotic peptoid synthesis can be used to efficiently generate diverse combinatorial libraries, allowing the screening of multiple peptoid sequences for a desired structure or activity.

Azapeptides are formed by the replacement of the $C^\alpha$ of amino acid residues with a nitrogen atom.

Oligocarbamates and oligoureas are sequence-specific oligomers that can have a variety of side chains.

Oligopyrrolinones have a stiffened backbone that incorporates 5-membered rings. Sequence-specific pentamers of oligopyrrolinones with a limited alphabet of proteinogenic sidechains can be synthesized using solution-phase methods. Short oligopyrrolinones adopt defined conformations and the oligopyrrolinone imino group can form intramolecular hydrogen bonds with the carbonyl group of an adjacent five-membered ring to give a structure that mimics β-strands, or can form intermolecular hydrogen bonds with the carbonyl on another oligomer to mimic a β-sheet.

N-methylated 3,5-linked pyrrolin-4-ones adopt a helix in solution and in the solid phase. Chiral vinylogous aminosulfonic acids are structured peptide mimics with an extended non-natural backbone that carries a strong negative charge, and can incorporate specific sequences of chiral sidechains.

β-peptides have a backbone differing from normal peptides by the presence of an additional methylene unit. γ-Peptides have two additional backbone methylene units, in comparison with natural peptides, and hence allow sidechain substitution of two different positions per monomer unit.

The examples below describe MLCK inhibitors that inhibit the growth of bacteria or are bactericidal. It is specifically envisaged that other bacteria may be susceptible to MLCK inhibitors in a similar manner as those described in the examples. It is well within the ability of one of ordinary skill in the art to screen and obtain other susceptible bacteria on which an MLCK inhibitor may have a similar effect.

MLCK inhibitors in accordance with the present invention are useful as active ingredients in pharmaceutical compositions for administration for the treatment of a variety of disorders associated with MLCK activity. These pharmaceutical compositions may have particular use in altering the permeability of an epithelial tight junction in vivo. A pharmaceutical composition is envisaged comprising an inhibitor having the general formula

A-B-C wherein B is covalently linked to A and C and wherein A and C each comprise at least two basic amino acids and B comprises Xaa1-Xaa2-Xaa3, wherein Xaa1 is selected from the group consisting of Tyr, Val, Lys, Gln, Phe, Ser, Pro, Thr, Asn, and Arg; Xaa2 is covalently bonded to Xaa1, and is selected from the group consisting of Lys, Val, Thr, Trp, His, Met, Asn, Ala, Glu, Phe, Gln, and Arg; and Xaa3 is covalently bonded to Xaa2, and is selected from the group consisting of Ala, Asp, Glu, Phe, Gly, Lys, Leu, Met, Asn, Pro, Gln, Arg, Ser, Thr, Val, and Tyr. Suitably, Xaa1 of B is selected from Tyr, Val, Lys, Gln or Phe; Xaa2 of B is selected from Lys, Val, Thr, Trp, or His; and Xaa3 of B is selected from Tyr, Met, Pro, Ser or Phe. Suitably, A and C may each comprise at least three basic amino acids.

The pharmacologically active inhibitors of this invention can be processed in accordance with conventional methods of pharmacy to produce pharmaceutical agents for administration to patients, e.g., in admixtures with conventional excipients such as pharmaceutically acceptable organic or inorganic carrier substances suitable for parenteral, enteral (e.g., oral), topical or transdermal application which do not deleteriously react with the active compounds.

Other conventional routes of administration, e.g., by subcutaneous, intravenous, intradermal, intramusclar, intramammary, intraperitoneal, intrathecal, intraocular, retrobulbar, intrapulmonary (e.g., term release), aerosol, sublingual, nasal, anal, vaginal, or transdermal delivery, or by direct injection at a particular site or regional delivery via intra arterial delivery or portal vein also is envisaged. The treatment may consist of a single unit does or a plurality of doses over a period of time. Ampoules are convenient unit dosages.

A unit dose is a discrete amount of a therapeutic composition dispersed in a suitable carrier. In certain embodiments, parenteral administration of the therapeutic compounds is carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

Suitable pharmaceutically acceptable carriers include, but are not limited to, water, salt (buffer) solutions, alcohols, gum arabic, mineral and vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic active compounds. If a pharmaceutically acceptable solid carrier is used, the dosage form of the analogs may be tablets, capsules, powders, suppositories, or lozenges. If a liquid carrier is used, soft gelatin capsules, transdermal patches, aerosol sprays, topical creams, syrups or liquid suspensions, emulsions or solutions may be the dosage form.

For parenteral application, particularly suitable are injectable, sterile solutions, preferably oily or aqueous solutions, as well as suspensions, emulsions, or implants, including suppositories. Ampoules are convenient unit dosages. The dosage of the MLCK inhibitors for parenteral administration is suitable between 1 to 300 mg per day, or an amount sufficient to maintain a dose of between 50 and 500 μM MLCK inhibitor in contact with the epithelium on a continuous basis.

For enteral application, particularly suitable are tablets, dragées, liquids, drops, suppositories, or capsules such as soft gelatin capsules. A syrup, elixir, or the like can be used wherein a sweetened vehicle is employed.

Sustained or directed release compositions can be formulated, e.g., liposomes or those wherein the active compound is protected with differentially degradable coatings, such as by microencapsulation, multiple coatings, etc. It is also possible to freeze-dry the MLCK inhibitors and use the lypholizates obtained, for example, for the preparation of products for injection. Transdermal delivery of pharmaceutical compositions of the analogs of formula (I) is also possible.

For topical application, there are employed as nonsprayable forms, viscous to semi-solid or solid forms comprising a carrier compatible with topical application and having a dynamic viscosity preferably greater than water. Suitable formulations include, but are not limited to, solutions, suspensions, emulsions, creams, ointments, powders, liniments, salves, aerosols, etc., which are, if desired, sterilized or mixed with auxiliary agents, e.g., preservatives, etc.

For direct administration of the MLCK inhibitors, e.g., delivered directly to a tumor, the dosage ranges between 5 mg to 1500 mg/dose, suitably, between 200-800 mg/dose.

The dosage forms may also contain adjuvants, such as preserving or stabilizing adjuvants. They may also contain other therapeutically valuable substances or may contain more than one of the compounds specified herein and in the claims in admixture.

As described hereinbefore, the MLCK inhibitors are preferably administered to human or animal patients in oral dosage formulation for the treatment of intestinal dysfunction. As an inhibitor in accordance with the present invention is released from the oral dosage formulation, it is absorbed into the intestinal cells, or from the intestine into the blood.

Oral administration is preferred for some diseases in which MLCK may play a role, such as intestinal diseases. Generally, a suitable amount ranges from 1 to 3000 mg per day, or sufficient to maintain a dose of between 50 and 500 μM inhibitor in contact with the epithelium on a continuous basis in a pharmaceutically acceptable carrier per unit dosage.

For example for the treatment of cancer and other tumor related disease the test group may receive from 0.1 mg to 500 mg/kg of body weight of the peptide-based drug per day by parenteral administration at the site of the cancer or tumor.

Those of ordinary skill in the art will readily optimize effective doses and co-administration regimens (as described hereinbelow) as determined by good medical practice and the clinical condition of the individual patient. Regardless of the manner of administration, it will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on age, sex, body weight, general state of health, on diet, on the timing and mode of administration, on the rate of excretion, and on medicaments used in combination and the severity of the particular disorder to which the therapy is applied. Dosages for a given patient can be determined using conventional considerations, e.g., by customary comparison of the differential activities of the subject compounds and of a known agent, such as by means of an appropriate conventional pharmacological protocol. A physician of ordinary skill can readily determine and prescribe the effective amount of the drug required to counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug. The dosage of active ingredient in the compositions of this invention may be varied; however, it is necessary that the amount of the active ingredient be such that an efficacious dosage is obtained. The active ingredient is administered to patients (animal and human) in need of treatment in dosages that will provide optimal pharmaceutical efficacy.

The total dose of therapeutic agent may be administered in multiple doses or in a single dose. In certain embodiments, the compounds or compositions are administered alone, in other embodiments the compounds or compositions are administered in conjunction with other therapeutics directed to the disease or directed to other symptoms thereof.

Suitably, compositions for administration directly to the lung are prepared, wherein the preferred route of administration is orally via an inhalant. An inhaler device is any device useful in the administration of the inhalable medicament. Examples of inhaler devices include nebulizers, metered dose inhalers, dry powder inhalers, intermittent positive pressure breathing apparatuses, humidifiers, bubble environments, oxygen chambers, oxygen masks and artificial respirators. It is particularly contemplated that the peptide inhibitors will be formulated as inhalable compositions. The compositions of the invention include kits in which the inhalable medicament is formulated in a container suitable for administration via inhalation.

The inhibitors used in the therapeutic methods of the present invention may be modified in order to improve their therapeutic efficacy via a decrease in toxicity, increase in circulatory time, or modification of biodistribution. A strategy for improving drug viability is the utilization of water-soluble polymers. (Greenwald et al., Crit Rev Therap Drug Carrier Syst. 2000; 17:101-161; Kopecek et al., J Controlled Release., 74:147-158, 2001).

Those of skill in the art are aware of PEGylation techniques for the effective modification of drugs. (Harris et al., Clin Pharmacokinet. 2001; 40(7):539-51). In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications. (Nathan et al., Macromolecules. 1992; 25: 4476-4484; Nathan et al., Bioconj Chem. 1993;4: 54-62).

The MLCK inhibitors may be delivered in a nonactive form, Linkers may be used to maintain the therapeutic agent in a pro-drug form until released from the backbone polymer by a specific trigger, typically enzyme activity in the targeted tissue. (See U.S. Pat. No. 6,673,574, herein incorporated by reference). For example, The MLCK inhibitor can be attached to a linker via proteolytic cleavage sites outside of the active core of the MLCK inhibitor. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the peptides described herein for therapeutic delivery.

Of course, it should be understood that the inhibitory peptides may form part of a therapeutic regimen in which the inhibitory peptide-based treatment is used in combination with a plurality of other therapies for the given disorder. As such, combination therapy is specifically contemplated.

EXAMPLES

The present invention is further explained by the following examples, which should not be construed by way of limiting the scope of the present invention.

Example 1

Synthesis and Characterization of MLCK Inhibitors

A. Synthesis of L- and D-Peptides

Peptide inhibitors were evaluated for MLCK inhibitory activity. The peptide inhibitors shown in Table 2 were synthesized as described below.

TABLE 2

| Sequence | Designation |
| --- | --- |
| Arg-Lys-Lys-Tyr-Lys-Tyr-Arg-Arg-Lys | PIK (SEQ ID NO: 12) |
| arg-lys-lys-tyr-lys-tyr-arg-arg-lys | D-PIK |
| lys-arg-arg-tyr-lys-tyr-lys-lys-arg | D-PIK(reversed) |
| Arg-Lys-Lys-tyr-lys-tyr-Arg-Arg-Lys | D-PIK(int.) |

Amino acids beginning with an uppercase letter designate L-amino acids.
Amino acids beginning with a lowercase letter designate D-amino acids.

Peptides were synthesized by solid-phase peptide synthesis techniques using Fmoc (9-fluorenylmethoxycarbonyl) chemistry using an automated Symphony Quartet Peptide Synthesizer (Zinsser analytic, Maidenhead). Arginine guanyl group were protected by 2,2,4,6,7-pentamethyldihydrobenzofuran-5-sulfonyl; lysine and tyrosine side chains of were protected by tert-butoxycarbonyl and tert-butyl, respectively. Rink amide MBHA resin 100 mg (0.78 mmol/g) was swollen with dichloromethane for 30 minutes. De-protection of Fmoc-amino acids was accomplished treatment with 20% (v/v) piperdine/dimethylformamide (DMF) for 20 min. Initial coupling reactions were performed by adding resin/amino acid/HOBt/PyBOP®/N,N, diisopropylethylamine (DIEA) in equivalents of 1/5/5/4.9/1 0 and mixing for 2 hours. Each subsequent coupling reaction was performed by N-α-Fmoc groups cleavage with 20% (v/v) piperdine/DMF for 12 minutes followed by mixing of 0.05 M Fmoc-amino acids dissolved in DMF with 0.1M of HBTU and 0.4M of 4-methylmorpholine for 30 min followed by resin washing in DMF. N-terminal acetylation was performed on some peptides prior to cleavage from the resin by treatment with 50% acetic anhydride, 25% pyridine and 25% DMF.

Crude peptides were cleaved from the resin for 3 hours in 95% trifluoroacetic acid (TFA), 2.5% triisopropylsilane and 2.5% H2O, roto-evaporated to remove solvents, precipitated with cold ether, dissolved with 2% acetonitrile 2% acetic acid and then lyophilised. Purification of desired peptides from crude material was achieved by semi-preparative HPLC using a Vydac 218TP C18 reversed-phase silica gel column (10×250 mm, 300 Å pore size, 5 μm particle size). Crude mixtures were separated using a 2% B to 50% B in 20 min gradient (flow rate=1 ml/min) where eluent A was 0.3% TFA in water and eluent B was 0.3% TFA in acetonitrile). Separation of crude peptide mixtures was monitored at 280 nm. Collected peptide fractions were pooled, concentrated and verified by liquid chromatography separation and mass spectrometry analysis (LC-MS). HPLC separation of peptides was performed on a 218TP C18 reversed-phase silica column (4.6×250 mm, 300 Å pore size, 5μ particle size) using a 2% B to 50% B in 20 min gradient (flow rate=0.5 ml/min) where eluent A was 0.1% TFA in water and eluent B was 0.1% TFA in acetonitrile). Peptides were monitored at 280 nm and by positive electrospray ionization performed using a Thermo Finnigan LCQ™ DECA mass spectrometer (MS) and analyzed using Thermo Finnigan Xcalibar™ software from (Thermo Separation Products, Riveria Beach, Fla.).

B. Peptide Inhibitors Inhibit MLCK in an in vitro Kinase Assay

The ability of a peptide to inhibit MLCK was determined according to Zolotarevsky et al., (2002) *Gastroenterology* 123:163-172. Briefly, confluent Caco-2 monolayers expressing the 215 kDa MLCK were used as the source of MLCK. Monolayers were harvested in lysis buffer (20 mM MOPS pH 7.4, 0.5% Triton X-100 (nonionic detergent), 0.5% NP-40, 1 mM DTT) with protease inhibitors and diluted to 0.1 mg/ml in kinase reaction buffer (20 mM MOPS, pH 7.4; 2 mM $MgCl_2$; 0.25 mM $CaCl_2$; and 0.2 µM calmodulin).

On ice, PIK (SEQ ID NO: 12) was diluted to various concentrations (0, 1, 10, 33, 100, and 330 µM) in kinase reaction buffer (20 mmol/L morhpolinepropanesulfonic acid, pH 7.4; 2 mmol/L $MgCl_2$; 0.25 mmol/L $CaCl_2$; and 0.2 µmol/L calmodulin), and the reaction was initiated by the addition of $\gamma^{32}P$-ATP (ICN, Costa Mesa, Calif.) and 5 µmol/L recombinant MLC. The mixtures then were transferred from ice to 30° C. for 5 to 30 minutes, such that the assay was in the linear range. MLC phosphorylation was determined by autoradiography of reaction mixtures separated by SDS-PAGE.

Addition of SEQ ID NO: 12 caused a dose-dependent inhibition of Caco-2 MLC kinase activity with an $IC_{50}$ of 29 µmol/L.

C. Inhibitors are Membrane Permeable

Membrane permeability is determined using an assay described in Zolotarevsky et al. *Gastroenterology* 123:163-172, (2002). Briefly, peptides are synthesized to include D-Biotin (Sigma, St. Louis, Mo.) at the amino terminus using an automated Pioneer Peptide Synthesizer (Applied Biosystems, Foster City Calif.). Caco-2 monolayers are incubated with 330 µM peptide in HBSS, rinsed to remove extracellular peptide, and fixed with 1% paraformaldehyde. The cells are then permeabilized with 0.1% Triton X-100 in phosphate-buffered saline (PBS) or not permeabilized. Biotinylated peptide is detected by incubation with Alexa 488-conjugated streptavidin (Molecular Probes, Eugene, Oreg.) in PBS with 1% bovine serum albumin. Stained monolayers are mounted in SlowFade reagent (Molecular Probes) and examiner by epifluorescence microscopy. Membrane permeability is indicated by a bright circumferential ring outlining each cell in permeabilized, but not nonpermeabilized preparations.

D. Inhibitors Inhibit MLCK in a Cell

Transepithelial resistance (TER), a sensitive marker of tight junction (TJ) permeability, was used to measure MLCK activity within cells.

The inhibitors may prevent actomyosin contraction or induce actomyosin relaxation in the cells. The effect of MLCK on actomyosin contraction caused a decrease in TER of cells grown in culture. Caco-2 cells expressing SGLT1 were maintained and grown as polarized monolayers on collagen-coated 0.4-µm film pore size polycarbonate membrane Transwell supports (Corning-Costar, Cambridge, Mass.). Monolayers were incubated with 500 µM of PIK, D-PIK, D-PIK(reversed), or D-PIK(int.) for one hour, after which transepithelial resistance (TER) was measured. Electrophysiologic measurements were made using agar bridges with Ag—AgCl calomel electrodes and a voltage clamp (University of Iowa Bioengineering, Iowa City, Iowa). Fixed 50 µA currents were passed across Caco-2 monolayers allowing TER to be calculated using Ohm's law. Fluid resistance was subtracted from all values before subsequent analysis.

Table 3 indicates that the tested peptides permeated the cells and were able to inhibit MLCK. Moreover, substituting the L-amino acids with D-amino acids had very little effect on the ability of the peptide to inhibit MLCK. Δ TER indicates the elevation in TER as compared to control Caco-2 monolayers. Also D-PIK and D-PIK (reversed) both produced similar increases in TER as acetylated PIK when compared with control monolayers, at concentrations up to 1 mM. These results demonstrate that inhibitor analogues produced using D-amino acids can produce the same physiological inhibition of MLCK as those produced using L-amino acids and that inhibitors containing D-amino acids are membrane permeant in a manner similar to PIK.

TABLE 3

| Inhibitor | Δ TER |
|---|---|
| PIK (SEQ ID NO: 12) | 45% +/− 5% |
| D-PIK | 41% +/− 9% |
| D-PIK(reversed) | 50% +/− 9% |
| D-PIK(int.) | 47% +/− 11% |

E. Specificity of PIK Analogues

Along with MLCK, PKA and CaMPKII are two other serine/threonine kinases that interact with calmodulin-mediated pathways. For stable MLCK inhibitors to be useful in vivo, it is important that they also selectively inhibit only MLCK.

cAMP-dependent protein kinase (PKA) activity was determined using a non-radioactive protein kinase assay kit by adding 20 units of PKA to 0.5, 1, 2.5 and 5 mM of MLCK inhibitor peptides and following manufacturer's instructions. The protein kinase inhibitor 6-22 amide was used as a positive control.

Calcium/calmodulin dependent protein kinase II (CaMPKII) activity was determined using a peptide pseudo-substrate (Biotin-PLSRTLSVSS-NH2) prepared by Fmoc solid-phase peptide synthesis as described previously (13). Biotinylated pseudo-substrate (0.5 µg/ml in PBS) was fixed to 96-well polystyrene microtiter plate wells previously coating with 100 µl of streptavidin (3 µg/ml in PBS) by overnight incubation at 4° C. Wells were then washed 3 times with 100 µl of TBS (PBS containing 0.05% Tween-20) to remove unbound pseudo-substrate peptide. CaMPKII (20 units) was mixed with 0, 0.5, 1, 2.5 or 5 mM of an MLCK inhibitor peptide in 108 µl of CaMPKII reaction buffer (50 mM Tris-HCl, 10 mM MgCl2 mM dithiothreitol, 0.1 mM Na2 EDTA, 100 µl ATP, 1.2 µM calmodulin and 2 mM CaCl2). After a 5 min pre-incubation at 30° C., 12 µl of kinase-MLCK inhibitor sample was added to pseudo-substrate-coated wells along with 100 µl of CaMPKII reaction buffer. After 20 min of incubation at 30° C., 100 µl of 20% $H_3PO_4$ was added and wells were washed 5 times with PBS. Phosphorylated pseudo-substrate was determined using a biotinylated monoclonal anti-phosphoserine antibody (100 µl of clone PSR-45, diluted 1/50,000 in PBS) followed by application of peroxidase-conjugated streptavidin and measurement of o-phenylenediamine (0.5 mg/ml) conversion (read at 492 nm).

Neither D-PIK nor D-PIK(reversed) nor D-PIK(int) demonstrated striking inhibitory effects toward PKA or CaMPKII at concentrations up to 5 mM. Thus, both D-PIK and D-PIK (reversed) were able to specifically inhibit MLCK, without affecting PKA or CaMPKII activities.

F. Susceptibility of Peptide Inhibitors to Intestinal Proteases

Peptides administered in vivo are susceptible to protease cleavage, particularly those administered to the intestine. PIK, D-PIK, D-PIK(reversed) and D-PIK(int.) were each incubated with rat intestinal fluid and also with Caco-2 intestinal epithelial cell extracts, which contain a mixture brush border and cytosolic proteases. Luminal intestinal secretions were obtained by flushing isolated rat intestines (duodenum to ileum) with 10 ml of 20 mM of N-2-Hydroxyethylpiperazine-N'-2-ethanesulfonic acid (HEPES) buffer, pH 7.4. Discharged contents were centrifuged to remove solids and the supernatant filtered through a 0.20 μm filter prior to determining total protein content. Confluent Caco-2 cells were rinsed with PBS, lifted by brief trypsin treatment into a small volume of Dulbecco's modified Eagles's medium (DMEM) and washed twice with phosphate buffered saline (PBS). The final cell pellet was re-suspended in a small volume of lysis buffer (50 mM Tris-HCL, 2 mM EDTA, 20% glycerol at pH 7.4) and sonicated on ice. Protein concentrations of isolated intestinal fluid and lysed Caco-2 cell extracts were determined using the Bio-Rad Protein Assay. Peptide inhibitors of MLCK (1 mg/ml) in PBS were mixed with 0.1 mg protein of intestinal secretions or Caco-2 cell lysate on ice and incubated for at 4° C. and 37° C., respectively. At selected times, 100 μl aliquots were withdrawn and mixed with an equal volume of 0.5% TFA (in 50/50 water/acetonitrile) to terminate enzymatic reactions. Samples were centrifuged and supernatants analyzed by LC-MS analysis to determine the cleavage pattern of PIK.

Residual peptide content was assessed by liquid chromatography-mass spectrometry (Tiller et al., *Anal Bioanal Chem* 2003;377:788-802) and positive ion electrospray ionization. In the presence of rat intestinal fluid, peptide bonds at the C-terminal sides of K and R residues of PIK were initially cleaved, at sites characteristic of trypsin-like endopeptidases. Extended incubations in rat intestinal fluid lead to the total hydrolysis of PIK. Caco-2 intestinal epithelial cell extracts cleaved PIK across the central palindromic sequence, and suggested the presence of a chymotrypsin-like endopeptidase.

The peptides listed in Table 2 (0.1 mg) were incubated with rat intestinal fluid (0.2 mg) at 37° C. for 0.5 min to 6 hours. The results are provided in Table 3 at $t_{1/2}$.

TABLE 3

| Inhibitor | $t_{1/2}$ |
|---|---|
| PIK | 0.2 min |
| D-PIK | 3.6 hours |
| D-PIK(reversed) | 13.4 hours |
| D-PIK (int.) | 0.2 min |

As demonstrated in Table 3, the inhibitor peptides containing all D-amino acids were significantly more resistant than a peptide having the same sequence but containing all L-amino acids. Surprisingly, the peptide containing all D amino acids and the reverse sequence of the L-amino acid-containing inhibitor peptide demonstrated even greater resistance without the loss of inhibitory activity (Table 3).

Example 2

Cells Infected by Enteropathogenic *Escherichia coli* Resist Disruption Upon Treatment with an Inhibitor of MLCK This example shows the effectiveness of the D-PIK(reversed) inhibitor of MLCK in preventing the disruption of the tight junction that occurs upon infection with enteropathogenic bacteria.

$T_{84}$ cells (polarized human intestinal epithelial cells) were grown in a 1:1 (vol/vol) mixture of Dulbecco-Vogt modified Eagle medium (Invitrogen, Carlsbad, Calif.) and Hams F-12 (Invitrogen) with 6% newborn calf serum (Invitrogen) at 37° C. in 5% CO2. Caco-2 cells were grown in high-glucose Dulbecco-Vogt modified Eagle medium supplemented with 10% fetal calf serum (Invitrogen) at 37° C. in 5% $CO_2$.

$T_{84}$ and Caco-2 monolayers were each infected with enteropathogenic *E. coli* (EPEC) strain E2348/69 at a multiplicity of infection (MOI) of 100. After 1 hour, medium was aspirated and replaced.

Control, EPEC-infected, and EPEC-infected+D-PIK(reversed) monolayers of $T_{84}$ and Caco-2 cells were fixed on glass coverslips with 3.7% paraformaldehyde and then permeabilized with 0.2% Triton X-100 for 15 minutes. Cells were incubated with 2.5% bovine serum albumin for 1 hour and then with primary antibody against occluding for 1 hour followed by rhodamine- or fluorescein isothiocyanate-conjugated secondary antibody for 1 hour. Monolayers were washed and mounted on glass microscope slides with Antifade reagent (Molecular Probes, Eugene, Oreg.). Stained monolayers were visualized and photographed with a Nikon Opti-Phot inverted microscope equipped with the Spot-RT digital imaging system (Diagnostic Instruments, Sterling Heights, Mich.). Transepithelial electrical resistance was measured four hours following infection with EPEC. D-PIK (reversed) was administered at 30, 100 and 300 μmol/L.

Visualization of the cells revealed that D-PIK(reversed) prevented redistribution of the tight junction transmembrane protein occludin following EPEC infection. D-PIK(reversed) also prevented a decrease in the transepithelial electrical resistance in EPEC infected cells. The D-PIK(reversed) inhibitor peptides may thus have therapeutic use against enteropathogenic bacteria.

Example 3

The Peptide Inhibitor of MCLK is Effective in Reversing Acute T-Cell Mediated TNF-Dependent Diarrhea This example demonstrates that protease resistant MLCK inhibitors are effective in vivo at treating a disease associated with MLCK activity. In this Example, the disease is acute diarrhea mediated by T-cell activation. Effectiveness of the peptide is determined by measuring net fluid secretion and blood-to-lumen flux of serum protein.

In vivo small intestinal permeability was determined in control mice and mice injected with anti-CD3 antibodies 90 minutes prior to the assay. 7-10 week old wild type C57BL/6, 210 kD MLCK–/– (45), or ΔF508 CFTR (36) female mice were mice were fasted for 12 or 24 hours prior to study and injected intraperitoneally with 200 μg anti-CD3 (clone 2C11) in 200 μl of PBS or vehicle alone. Mice were then used for intestinal permeability assays or sacrificed for tissue harvest. Harvested tissues were snap frozen in OCT for immunofluorescence, placed in Trizol (Invitrogen) for mRNA analysis, or used for epithelial cell isolation, as described below. All animal experiments were carried out in accordance with National Institutes of Health guidelines under protocols approved by the Institutional Animal Care and Use Committee at the University of Chicago. Intestinal permeability assay. Intestinal permeability and water flux was measured by adapting an in vivo assay previously used in rats. 7-9 week old female mice were fasted for 24 hours prior to each experiment. Anesthesia was induced 1 hour after treatment with anti-CD3 or vehicle with ketamine (75 mg/kg, intraperitoneal injection, Fort Dodge) and xylazine (25 mg/kg, intraperitoneal injection, Lloyd Laboratories). Mice were injected intravenously or retroorbitally with 250 µl of 1 mg/ml Alexa 488 conjugated bovine serum albumin (Molecular Probes) and anesthesia induced. The abdomen was opened by a midline incision and a 4-5 cm loop of jejunum was cannulated at the proximal and distal ends with 0.76 mm internal diameter polyethylene tubing. Flushing solution (140 mM NaCl, 10 mM HEPES, pH 7.4) warmed to 37° C. was first perfused through the jejunal loop at 1 ml/min for 10 minutes using a peristaltic pump (BioRad). This was followed by perfusion of 5 ml test solution (50 mM NaCl, 5 mM HEPES, 2 mM sodium ferrocyanide, 2.5 mM KCl, 20 mM glucose, pH 7.4) in a recirculating manner at 1 ml/min for 3 hours, beginning 90 minutes after anti-CD3 or vehicle treatment. The abdominal cavity was covered with moistened gauze and body temperature, measured via rectal thermometer, was maintained at 37° C. using a heating lamp. For experiments involving Na+ free perfusate, N-methyl-D-glucamine-Cl was substituted for NaCl. Alternatively, inhibitors were added to the perfusate when required, including D-PIK(reversed) and D-PIK (25-250 µM). 1 ml aliquots of test solution were removed at the beginning and end of the perfusion. After perfusion, the animal was sacrificed and the perfused jejunal segment excised and the length was measured. The excised intestinal loop was then snap frozen in OCT or used for epithelial cell isolation. Ferrocyanide concentration in the perfusate was measured using a previously described colorimetric assay (Sadowski and Meddings, *Can J Physiol Pharmacol* 1993;71: 835-9). Since ferrocyanide cannot cross tight junctions, its concentration reflects movement of water into or out of the luminal perfusate. Alexa 488 conjugated bovine serum albumin concentration was measured using a microplate reader (Synergy HT, Bio-Tek Instruments, Inc.) using an excitation wavelength of 485 nm and an emission wavelength of 528 nm. BSA movement into the luminal perfusate was determined by quantitative fluorescence using an excitation wavelength of 485 nm and an emission wavelength of 528 nm. Preliminary quantitative SDS-PAGE analysis showed that Alexa 488 fluorescence accurately represented the content of intact bovine serum albumin in the luminal perfusate. Probe clearance was calculated as: $Cprobe=(C_iV_i-C_fV_f)/(C_{avg}TL)$; water flux was calculated as: $(V_i-V_f)/(TL)$. In these equations, $C_i$ is the measured initial probe concentration; $C_f$ is the measured final probe concentration; $V_i$ is the measured initial perfusate volume; $V_f$ is calculated as $V_i([ferrocyanide]_i/[ferrocyanide]_f)$; $C_{avg}$ is calculated as $(C_i-C_f)/\ln(C_i/C_f)$; T is hours of perfusion; and L is the length of the perfused jejunal section in cm.

Anti-CD3 treatment, which causes acute TNF-mediated diarrhea in these animals (Musch et al. *J Clin Invest* 2002; 110:1739-47), was found to be associated with net fluid secretion, rather than absorption. Injection of anti-CD3 antibodies into mice caused fluid to enter the small intestine, whereas control mice not receiving anti-CD3 antibodies absorbed fluid from the small intestine. Systemic T cell activation induced by administration of anti-CD3 antibodies caused acute diarrhea in mice. Cytokine induction of diarrhea in response to administration of anti-CD3 antibodies was confirmed by measuring an increase in mucosal interferon-γ and TNF-α transcripts and in the weight to length ratio of the small intestine. Gross evidence of intestinal inflammation, including vasodilation, injection, and edema was also present. Thus anti-CD3 injection was an effective means of inducing an acute, self-limited, immune-mediated diarrhea in mice.

Administering a peptide inhibitor of MLCK, D-PIK(reversed), at different concentrations (25, 80, and 250 µmolar) reduced or reversed the effect of the anti-CD3 antibody in mice in a dose dependent manner. Injection of anti-CD3 antibodies into mice caused an increase in leakage of proteins from the blood into the intestinal lumen. In this example, fluorescently-tagged bovine serum albumin (BSA) injected into the blood stream was recovered in the lumen of the small intestine. T cell activation with anti-CD3 increased the amount of BSA leakage, compared to control mice not receiving anti-CD3 antibodies. Administration of D-PIK(reversed) at different concentrations (25, 80, and 250 µmolar) reduced or prevented the effect of the anti-CD3 antibody on the level of BSA in the intestine in a dose dependent manner. When D-PIK (reverse) was included in the luminal perfusate at the concentrations indicated, a dose-dependent reversal of fluid secretion and protein leakage was seen. These data indicate that the peptide inhibitor is able to reverse both intestinal permeability defects and diarrhea in vivo.

Corroboration of the capacity of D-PIK(reversed) to reverse net fluid secretion and blood to lumen flux of BSA in anti-CD3 treated cells is provided in the following observations. First, the diarrhea and barrier defects associated with systemic T cell activation were not due to malabsorption of $Na^+$ or secretion of $Cl^-$. Blocking NHE2 and NHE3 dependent $Na^+$ absorption in the absence of CD3 treatment did not reverse net water movement to cause secretion nor cause increased paracellular flux of BSA. Mice mutant for the chloride transporter CFTR (CFTRΔF508) displayed the same net fluid secretion and blood to lumen flux of BSA as wild type mice upon CD3 treatment. Secondly, the barrier dysfunction caused by CD3-treatment was not due to mucosal ulceration or epithelial apoptosis, but rather occurred in the presence of an intact epithelial layer. Thirdly, distribution of the tight junction protein occludin in tissue in vivo was altered, and the cytoplasmic plaque tight junction protein ZO-1 was visualized as thinner and more sinuous following anti-CD3 treatment. Fourthly, changes in the morphology of the tight junction and the perijunctional cytoskeleton could be observed in anti-CD3 treated mice, which showed an increased cytoplasmic density surrounding the tight junction, consistent with cytoskeleton condensation. Fifthly, myosin light chain phosphorylation, as detected by immunofluorescence and by SDS-PAGE immunoblot of isolated intestinal epithelial cells, increased more than 3 fold in the perijunctional ring of jejunal villus enterocytes 3-hours after injecting mice with anti-CD3, before falling: the changes correlated with the development and resolution of diarrhea. Sixthly, mice lacking MLCK (210 KDa) were protected from diarrhea induced by anti-CD3 injection.

In this example D-PIK(reversed) was used. However, D-PIK was found to function in a similar manner and it is expected that MLCK inhibitors having D-amino acids, L-amino acids or non-hydrolyzable bonds would have use in reversing acute T-Cell mediated TNF-dependent diarrhea.

Example 4

The Peptide Inhibitor of MCLK Inhibits the Growth of Bacteria and is Bactericidal Liquid cultures of JM109 lab strain *E. coli* or ATCC *E. coli* strain 35150 (O157 hemolytic) were cultivated to mid-log phase. D-PIK (reverse) peptide, or an L-scrambled peptide were added at final concentrations of from zero to 200 µm, and optical density at 600 nm was measured at various time points using a spectrophotometer. The L-scrambled peptide contained the same number of amino acid residues, and comprised the same amino acid content, as the D-PIK (reverse), but the amino acids of the L-scrambled peptide were L isoforms and were in a random, scrambled order. Growth of JM109 was inhibited at 150 or 200 µM by D-PIK (reverse) or L-scrambled peptide, with up to a 5.5 fold decrease in optical density over several hours. O157 hemolytic *E. coli* showed a dose-dependent D-PIK (reverse), but not L-scrambled peptide inhibition of growth overnight. Colony forming units were determined from serial dilutions of the D-PIK (reverse)-treated cultures, incubated on plates after 21 hours after administration of the inhibitor. Lower culture turbidity was shown to be a good marker for growth inhibition by colony forming unit assay. Of cultures treated with 100 and 200 µM D-PIK (reverse), JM109 *E. coli* showed a 2-log kill or greater compared to untreated and L-scrambled treated cells.

D-PIK (reverse) treated JM109 cells were incubated with two nuclear stains, SYTO 9 and propidium iodide. Permeabilized cells allow propidium iodide to enter, where it quenches the SYTO9 signal. Treated cells were either visualized by fluorescence microscopy or fluorescence was quantified by fluorospectrophotometry. Quantification of cell death at 200 µM D-PIK (reverse), revealed less than 10% cells were live after 15 minutes of treatment, demonstrating the bactericidal mode of action of D-PIK (reverse). Microscopy of D-PIK (reverse)-treated cells revealed large clumps of bacteria with live cells surrounding a dead core, which suggests a D-PIK (reverse)-mediated cell division defect (through inhibition of a myosin homologue) that prevents younger generations from separating from their division predecessors. Fluorescent microscopy of biotinylated D-PIK (reverse)-treated JM109 showed D-PIK (reverse) to localize both to cell division septa and to peripheral clumps.

For electron microscopy JM 109 *E. Coli* were treated with 50 µM biotinylated D-PIK (reverse), fixed for 15 min or 2 h in either 2% paraformaldehyde/1% glutaraldehyde or Periodate Lysine Paraformaldehyde Fixative and treated with Alexa Fluor®* 594 FluoroNanogold. After visualization by fluorescent microscopy and post-fixation with 1% glutaraldehyde for 1 hour, samples were developed by silver precipitation until a sample was visualized by light microscopy to be brown in color. Electron microscopy showed binding of D-PIK (reverse) to both the outer membrane/periplasm and the cortical cytoplasm. Cytoplasmic enhancement showed proximity of D-PIK (reverse) to filaments.

In this example D-PIK(reversed) was used. However, D-PIK, PIK and D-PIK(int) were found to function in a similar manner. It is expected that MLCK inhibitors having D-amino acids, or non-hydrolyzable bonds would have use in inhibiting the growth or in killing bacteria.

Example 5

The Peptide Inhibitor of MCLK Regulates the Contraction of the Actin Ring During Purse String Wound Closure In this example, it is envisaged that an inhibitor comprising a D-amino acid or a non-hydrolysable bond would function in the same way as a peptide comprising L-amino acids.

A. Materials and Methods

Caco-2 BBe cells expressing an EGFP-β-actin fusion protein were maintained and monolayers grown on rat tail collagen-coated 35 mm cell culture dishes. Dishes were placed on a 37° C. heated stage in pH 7.4 HEPES-buffered HBSS (without bicarbonate) during wounding and subsequent imaging. Monolayers were treated with 10 µM Y-27632 (Calbiochem, San Diego, Calif.) or 250 µM PIK, prior to wounding. Wounds were created manually using a 0.003 gauge tungsten wire.

Wound closure in live cells was imaged using an epifluourescence microscope equipped with an Endow GFP bandpass emission cube and Roper Coolsnap HQ camera controlled by MetaMorph 6 (Universal Imaging Corporation, Downingtown, Pa.). Serial z-stack images, at 1 µm intervals, were obtained every 2 min after wounding. Fixed wounds were imaged after staining using a quad bandpass 88000 filter set (Chroma Technology). Wound areas were determined using MetaMorph 6 after manually tracing the wound edge. Pixel intensities were determined with MetaMorph 6 using matched samples stained and imaged under identical conditions. For these analyses pixel intensities along lines perpendicular to the wound edge were plotted. The peak actin intensity, corresponding to the developing or established actin ring, was used to align multiple lines and was arbitrarily designated 0. These analyses were performed for multiple wounds.

Wounds were fixed in 1% paraformaldehyde in PBS at indicated times after wounding. Wound sites were labeled stereotactically to aid in identifying specific wounds after staining. After permeabilization with 0.1% Triton X-100, specific antibodies were applied. Activated rho was detected by incubation with a GST-rhotekin rho binding domain fusion protein (Upstate Biotechnology, Lake Placid, N.Y.) followed by incubation with polyclonal goat anti GST and then Alexa 594 donkey anti-goat IgG. Control experiments showed that substitution of GSTrhotekin with an irrelevant GST fusion protein did not label the wound edge but did nonspecifically label dead/damaged cells within the wound. ROCK was labeled using a mouse monoclonal anti-ROCK-I/ROK-β antibody (Becton-Dickinson) followed by Alexa-594 goat anti-mouse IgG. MLCK was detected using mouse monoclonal anti MLCK clone K-36 (Sigma, St. Louis, Mo.) followed by Alexa-594 goat anti-mouse IgG. Phosphorylated MLC was detected using affinity-purified polyclonal rabbit antisera, followed by Alexa-350 goat anti-rabbit antibody (Molecular Probes). In fixed preparations, F-actin was stained using Alexa-488-phalloidin. Activated MLCK was detected using biotinylated PIK and Alexa-594 streptavidin. Labeling of the inhibitor was assessed quantitatively using a fluorescent microplate reader.

Kinase assays were performed as described in example 1, using long MLC kinase from Caco-2 cells and recombinant intestinal epithelial MLC. PIK or vehicle was added to reaction mixtures and the reaction initiated by the addition of γ32P-ATP and 5 µM recombinant MLC. MLC phosphorylation was determined by SDS-PAGE autoradiography of reaction mixtures.

B. Results

When the contraction phase of wound closure began in Caco-2 intestinal epithelial cells, phosphorylated MLC colocalized with the contracting actomyosin ring and MLCK decorated the actomyosin ring in a punctate pattern. MLCK activation at the wound site was shown using a morphological PIK probe developed to be specific for activated MLCK. PIK was found to bind to active, but not inactive, aldehyde-fixed MLCK, and a biotinylated PIK peptide probe allowed localization of PIK binding using fluorescent streptavidin conjugates. The efficacy of the PIK probe was tested: the PIK probe preferentially bound to the perijunctional actomyosin ring, a site enriched in MLC phosphorylated by MLCK, and graduated induction of MLCK gene expression in Caco-2 cells resulted in increased PIK labeling that correlated closely with the extent of MLCK catalytic subunit expression ($r^2$=0.98). Using the biotinylated PIK probe, activated MLCK was detected when the contraction phase began within discrete foci at the wound edge. Recruitment and activation of MLCK is thus correlated with contraction during purse-string wound closure. A similar MLCK-dependent process was found to be involved in the healing of oligocellular wounds in vivo, in rapidly-fixed biopsies of human colonic mucosa. The MLC phosphorylation mechanism of wound closure is thus active in vivo.

PIK inhibition of MLCK did not prevent actomyosin ring assembly, but did cause contraction of the assembly to stall. The actin ring began to fragment, wound edges became irregular, rather than rounded, and the wound returned to its original area. PIK can therefore be used to regulate contraction during pursestring wound closure. An analysis of pursestring wound closure of individual cells also showed a potential regulatory role for PIK. Individual cells in an intact monolayer were destroyed with a current pulse delivered from a microelectrode, resulting in a local current leak, whose magnitude decreased exponentially as the barrier was restored. Inhibition of MLCK with PIK resulted in a marked slowing of repair. Between 2 min and 8 min after creating the lesion, the local current leak decreased by only 36% compared with 53% in control monolayers. This corresponds to a 74% increase in the time constant for recovery. Therefore, like larger wounds, purse-string closure of single-cell wounds requires MLCK activity, which can be regulated by the addition of PIK.

Example 6

The Peptide Inhibitor of MCLK Inhibits the Growth of Tumor Cells

Tumors of mice with were injected with saline or saline plus 0.5 mg D-PIK (reverse), every other day. After 3 injections, the mice were sacrificed and the size of the tumors was recorded. A statistically significant (p<0.05) difference in tumor size between saline and D-PIK (reverse) injected groups was noted. Microscopic examination of sections of the tumors revealed that significant necrosis had occurred in the tumors that had been injected with D-PIK (reverse). It is envisioned that the inhibitors, particularly in a stable form, may be used to therapeutically treat cancers.

In this example D-PIK(reversed) was used. However, D-PIK, PIK and D-PIK(int) were also found to function in a similar manner. It is expected that MLCK inhibitors having D-amino acids, L-amino acids or non-hydrolyzable bonds would cause necrosis of tumor cells and a reduction in tumor size.

Example 7

The Peptide Inhibitor of MCLK Affects Cell Migration

A biotinylated PIK probe specific for MLCK, described in example 5, was used to determine whether an inhibitor could function to inhibit MLCK in migrating cells. The biotinylated PIK peptide allowed localization of PIK binding using fluorescent streptavidin conjugates. To confirm that the biotinylated PIK probe functioned adequately, it was shown to preferentially bind to a site enriched in MLC phosphorylated by MLCK, the perijunctional actomyosin ring, in intact epithelial monolayers. The biotinylated PIK was also shown to highly concentrate within lamellipodia in migrating Caco-2 cells, demonstrating that MLCK is activated in migrating cells. A role for the inhibitors in regulating the migration of cells is implicated.

Cell migration is required for embryonic development, tumor formation, and metastasis. It is envisioned that inhibitors of the instant invention would inhibit cell migration and can be used to therapeutically treat diseases that require cell migration, including cancer, metastasis and tumor related diseases, and also to control embryonic development.

Example 8

Treatment of Inflammatory Bowel Disease.

A clinical trial is conducted in which five to fifty subjects are selected for the clinical study. The patients suffer from inflammatory bowel disease. The subjects are divided into two groups, one of which receives the inhibitory fragment as the active agent and the other receives a placebo. Subjects in the test group receive between 1 and 3000 mg of the inhibitory peptide-based drug per day by the oral route. The subjects are maintained on this therapy for 3-12 months. Accurate records are kept as to the number and severity of the symptoms in both groups and at the end of the study these results are compared. The results are compared both between members of each group and also the results for each patient are compared to the symptoms reported by each patient before the study began. The results demonstrate that patients in the test group have reduced bowel distress compared to the control group and compared to the test members symtomalogy at the beginning of the study.

It will be appreciated that the pharmaceutical compositions and treatment methods of the invention are useful in fields of human medicine and veterinary medicine. Thus the subject to be treated is a mammal, such as a human or other mammalian animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese. Other subjects to be treated include non-mammals, such as birds, fish, amphibians and reptiles.

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

All patents, publications and references cited herein are hereby fully incorporated by reference. In case of conflict between the present disclosure and incorporated patents, publications and references, the present disclosure should control.

The invention claimed is:

1. An inhibitor of myosin light chain kinase comprising SEQ ID NO: 13 and having at least one amino acid that is a D-amino acid, wherein the inhibitor having at least one D-amino acid retains at least substantially the same biological activity relative to the same inhibitor having all L-amino acids and wherein said inhibitor has an amino acid sequence of 9 to 120 amino acids.

2. The inhibitor of claim 1, wherein the inhibitor comprises at least three D-amino acids.

3. The inhibitor of claim 1, wherein the inhibitor comprises from 10% to 100% D-amino acids.

4. A pharmaceutical composition comprising the inhibitor of claim 1 and a pharmaceutically acceptable carrier.

5. The inhibitor of claim 3, wherein the inhibitor comprises 100% D-amino acids.

6. The pharmaceutical composition of claim 4, wherein the inhibitor comprises at least three D-amino acids.

7. The pharmaceutical composition of claim 4, wherein the inhibitor comprises from 10% to 100% D-amino acids.

8. The pharmaceutical composition of claim 7, wherein the inhibitor comprises 100% D-amino acids.

* * * * *

UNITED STATES PATENT AND TRADEMARK OFFICE
CERTIFICATE OF CORRECTION

| | |
|---|---|
| PATENT NO. | : 7,585,844 B2 |
| APPLICATION NO. | : 11/111463 |
| DATED | : September 8, 2009 |
| INVENTOR(S) | : Turner et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 817 days.

Signed and Sealed this

Fourteenth Day of December, 2010

David J. Kappos
*Director of the United States Patent and Trademark Office*